US009815059B2

(12) United States Patent
Pesen Okvur

(10) Patent No.: US 9,815,059 B2
(45) Date of Patent: Nov. 14, 2017

(54) MICROFLUIDIC DEVICE FOR INVESTIGATION OF DISTANCE DEPENDENT INTERACTIONS IN CELL BIOLOGY

(71) Applicant: Devrim Pesen Okvur, Izmir (TR)

(72) Inventor: Devrim Pesen Okvur, Izmir (TR)

( * ) Notice: Subject to any disclaimer, the term of this patent is extended or adjusted under 35 U.S.C. 154(b) by 0 days.

(21) Appl. No.: 15/027,700

(22) PCT Filed: Sep. 29, 2014

(86) PCT No.: PCT/EP2014/070839
§ 371 (c)(1),
(2) Date: Apr. 7, 2016

(87) PCT Pub. No.: WO2015/052034
PCT Pub. Date: Apr. 16, 2015

(65) Prior Publication Data
US 2016/0243551 A1    Aug. 25, 2016

(51) Int. Cl.
*B01L 3/00* (2006.01)
*G01N 33/50* (2006.01)

(52) U.S. Cl.
CPC ... *B01L 3/502761* (2013.01); *B01L 3/502776* (2013.01); *G01N 33/502* (2013.01); *G01N 33/5008* (2013.01); *G01N 33/5029* (2013.01); *B01L 2200/0647* (2013.01); *B01L 2300/0816* (2013.01); *B01L 2300/0861* (2013.01); *B01L 2300/10* (2013.01); *B01L 2300/12* (2013.01); *B01L 2300/168* (2013.01); *B01L 2400/086* (2013.01)

(58) Field of Classification Search
CPC .......... B01L 3/502761; B01L 2300/12; B01L 2300/0861; B01L 2200/0647; B01L 2300/168; G01N 33/502
See application file for complete search history.

(56) References Cited

U.S. PATENT DOCUMENTS

| | | | | |
|---|---|---|---|---|
| 6,267,858 | B1 * | 7/2001 | Parce et al. .......... | B01J 19/0093 204/451 |
| 6,416,642 | B1 * | 7/2002 | Alajoki et al. ....... | B01J 19/0093 204/451 |
| 6,432,630 | B1 * | 8/2002 | Blankenstein ......... | B01D 57/02 422/186 |
| 2002/0146822 | A1 * | 10/2002 | Takayama et al. .... | C12N 5/069 435/375 |

(Continued)

FOREIGN PATENT DOCUMENTS

WO    WO2012050981 A1    4/2012

OTHER PUBLICATIONS

Feng Guo et al "Probing cell-cell communication with microfluidic devices", Lab on a Chip, vol. 13, No. 16, Jan. 1, 2013, pp. 3152.

(Continued)

*Primary Examiner* — Gautam Prakash
(74) *Attorney, Agent, or Firm* — Gokalp Bayramoglu

(57) ABSTRACT

The invention presents a microfluidic device that provides investigation of distance dependent interactions between cells and various factors. A method that uses the device to determine distance dependent interactions between cells and various factors and agents that can change these interactions is also presented.

15 Claims, 4 Drawing Sheets

(56) References Cited

U.S. PATENT DOCUMENTS

2003/0138941 A1* 7/2003 Gong et al. .......... B01L 3/5027
                                                                           435/287.2

OTHER PUBLICATIONS

Sasa Trkov et al "Micropatterned three-dimensional hydrogel system to study human endothelial-mesenchymal stem cell interactions", Journal of Tissue Engineering and Regenerative Medicine, vol. 4, No. 3, Mar. 1, 2010, pp. 205-215.

Yi-Chin Toh et al "A novel 3D mammalian cell perfusion-culture system in microfluid channels", Lab on a Chip, vol. 7, No. 3, Jan. 1, 2007, pp. 302.

* cited by examiner

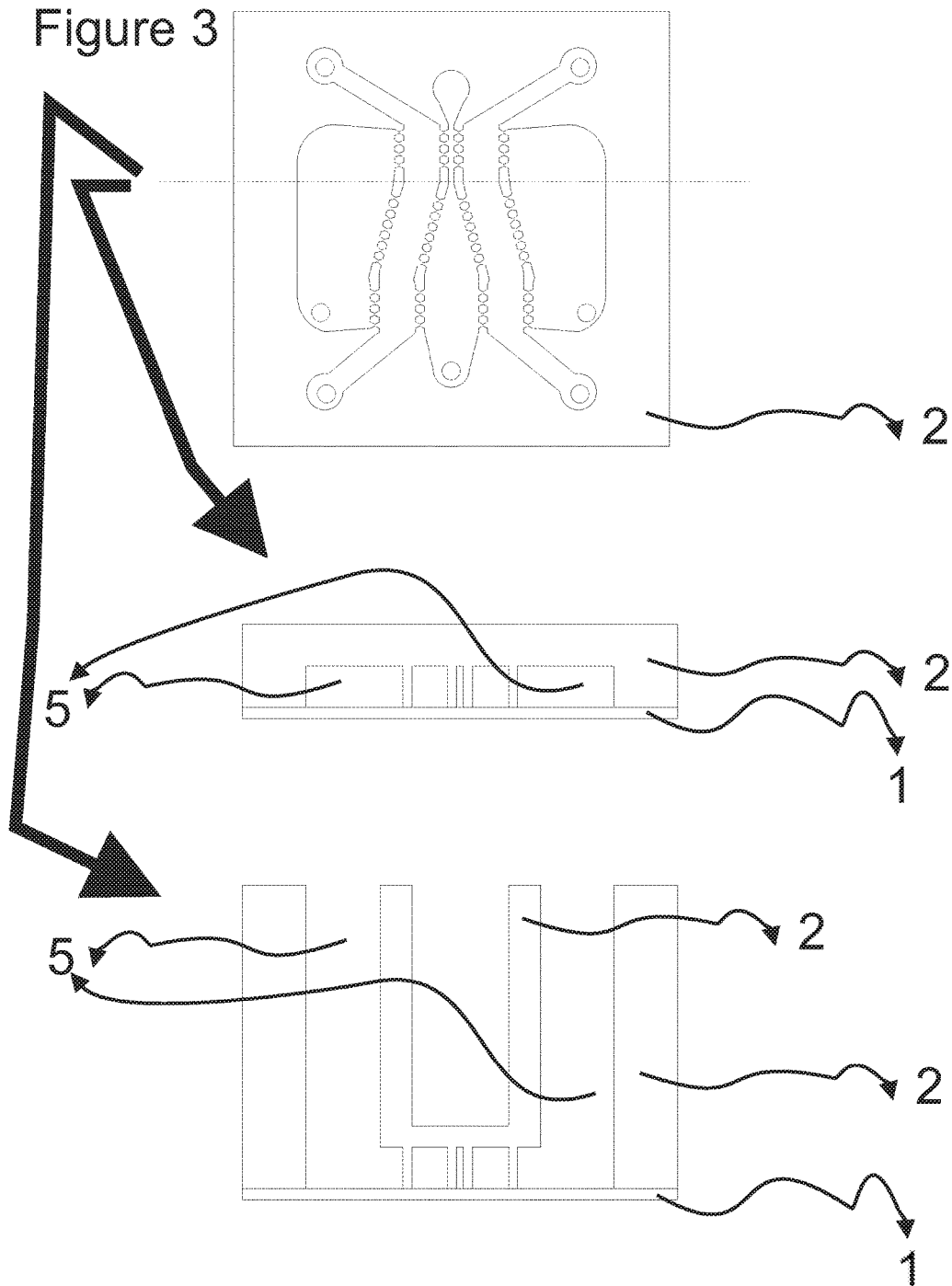

MICROFLUIDIC DEVICE FOR INVESTIGATION OF DISTANCE DEPENDENT INTERACTIONS IN CELL BIOLOGY

FIELD OF THE INVENTION

The invention concerns a microfluidic device that determines the distance dependent interactions between various factors such as cells which are matrix embedded or not and same type of cells which are matrix embedded or not, another type of cells which are matrix embedded or not, different and more than one type of cells which are matrix embedded or not, a matrix with different stiffness, a different type of matrix, culture medium, physiological buffer solution, a biological or chemical molecule, a soluble or matrix bound component or a combination thereof, and a method to determine these interactions and a method to determine agents that affect these interactions.

BACKGROUND OF THE INVENTION

Interactions of cells with factors such as same or different types of cells, soluble factors or matrix bound soluble factors, depend on the distances between cells and the factors. For example, breast cancer cells that express epidermal growth factor receptor move towards the source of epidermal growth factor source. Different cells can show different interaction mechanisms such as autocrine, juxtacrine, paracrinem endocrine signaling. Cells can give chemotactic, haptotactic, durotactic responses to different factors. Research in cancer, stem cells, immunology, development, endocrinology, neuroscience etc. require better devices that can investigate interactions of cells with factors such as those mentioned above.

Microfluidics Microfluidic technology provides precise spatial and temporal control, high-throughput analysis, low fabrication costs ve portability. Used material and waste volumes can be as low as picoliters. Using small volumes of unknown or toxic materials provides safe experimental study. Moreover, microfluidic technology can provide means to mimic physiological microenvironments. This feature can help us more realistically study cells in both health and disease states and improve drug testing approches it can also help reduce animal testing.

Devices used today usually focus on providing gradients of soluble factors (Kamm, R. D. et al. Device for High Throughput Investigations of Cellular Interactions. PCT/US2011/054029 2011). However, in vivo, gradients are generated by the sources of factors and agents to be responded to being at different distances. The device of this patent application positions the cells and factors to be investigated at different, distances from each other and thus provides a more physiological setup. In addition the device of this patent application allows simultaneous investigation of different distances in one device

SUMMARY OF THE INVENTION

The purpose of the invention is to determine distance dependent interactions of cells with various factors. Another purpose of the invention is to test agents that can affect distance dependent interactions of cells with various factors.

The microfluidic device with the described features is shown in the drawings below.

The drawings are not necessarily to scale.

BRIEF DESCRIPTION OF THE DRAWINGS

FIG. 3 shows the longitudinal view of the microfluidic device.

BRIEF DESCRIPTION OF THE REFERENCES IN THE DRAWINGS

Figure 1A:
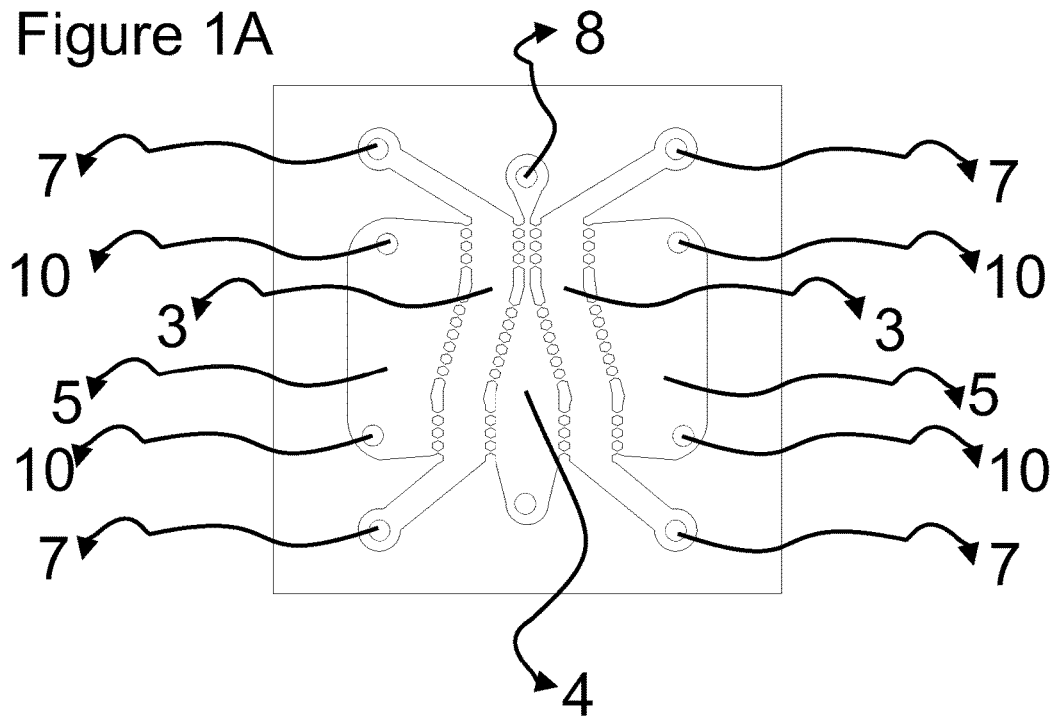
FIG. 1A shows the top view of a first embodiment of the microfluidic device.

Parts in the figures are numbered and their explanations are given below:
1. Optically transparent surface
2. Structure
3. Test channel
4. Main channel
5. Fluid reservoir
6. Post
7. Test channel opening
8. Main channel opening
9. Shared test and main channel opening
10. Fluid channel opening
11. Wide fluid channel opening

DETAILED DESCRIPTION OF THE INVENTION

The invention is a microfluidic device that determines the distance dependent interactions of cells with factors such as same or different types of cells, soluble factors, matrix bound factors.

In one embodiment, the device has two main parts: Optically transparent surface (1) and a structure (2) on this optically transparent surface. This structure (2) comprises, separated by posts (6), two test channels (3), one main channel (4), the width of which can be constant at different regions and increases continuously or in steps along its length in one direction, neighboring and in the middle of the test channels (3), two fluid reservoirs (5) each neighboring a test channel (3), four test channel openings (7), two main channel openings (8) and four fluid reservoir openings (10) (FIG. 1A).

Figure 1B:
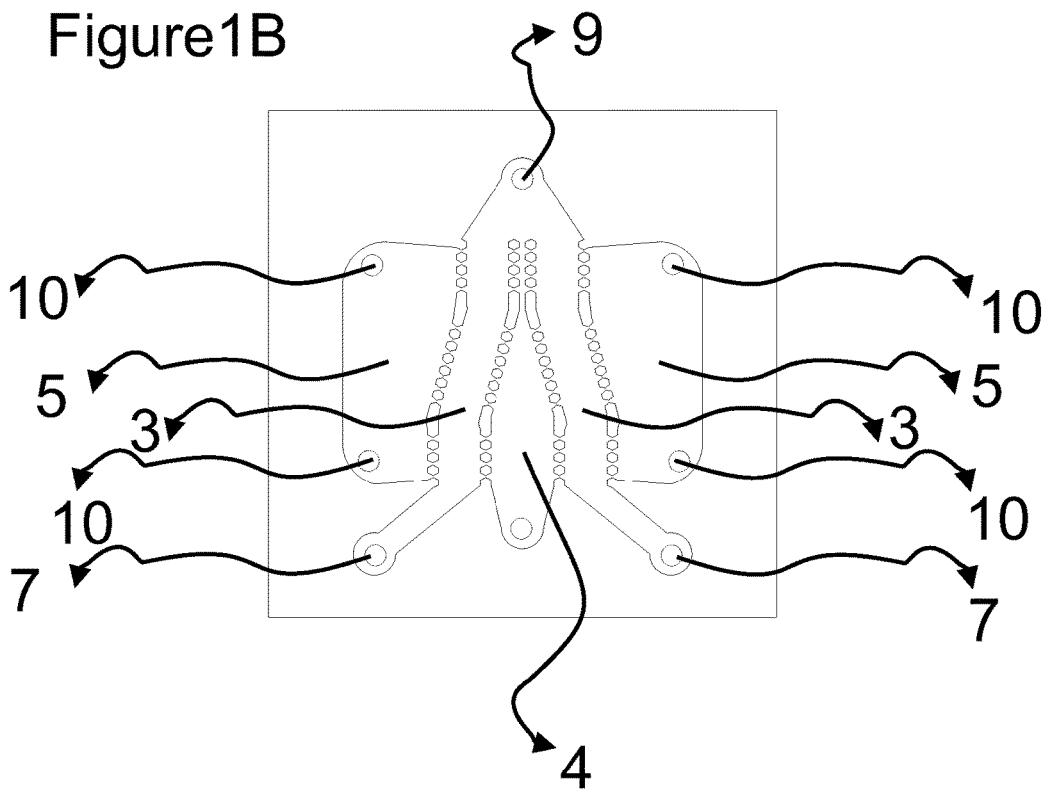
FIG. 1B shows the top view a second embodiment of the microfluidic device.

In another embodiment, the device has two main parts: Optically transparent surface (1) and a structure (2) on this optically transparent surface. This structure (2) comprises, separated by posts (6), two test channels (3), one main channel (4), the width of which can be constant at different regions and increases continuously or in steps along its length in one direction, neighboring and in the middle of the test channels (3), two fluid reservoirs (5) each neighboring a test channel (3), two test channel openings (7), one main channel opening (8), one shared test and main channel opening (9) and four fluid reservoir openings (10) (FIG. 1B).

Figure 1C:
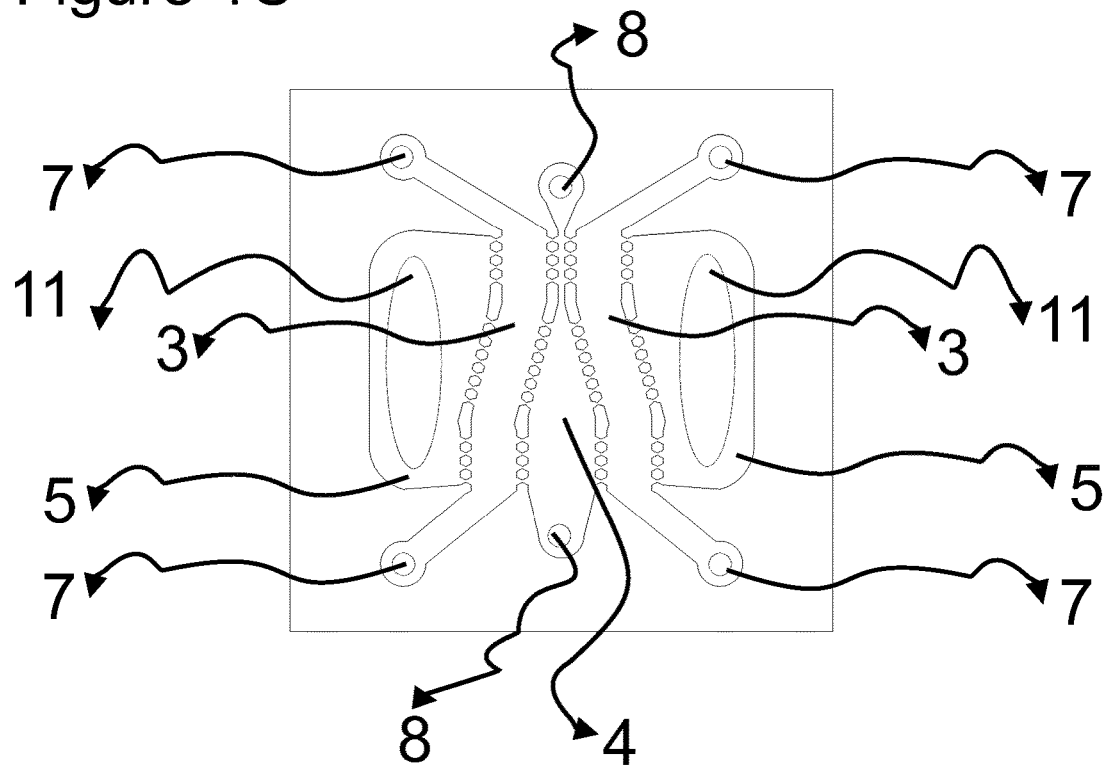
FIG. 1C shows the top view a third embodiment of the microfluidic device.

In another embodiment, the device has two main parts: Optically transparent surface (1) and a structure (2) on this optically transparent surface. This structure (2) comprises, separated by posts (6), two test channels (3), one main channel (4), the width of which can be constant at different regions and increases continuously or in steps along its length in one direction, neighboring and in the middle of the test channels (3), two fluid reservoirs (5) each neighboring, a test channel (3), four test channel openings (7), two main channel openings (8) and two wide fluid reservoir openings (11) (FIG. 1C)

Figure 1D:
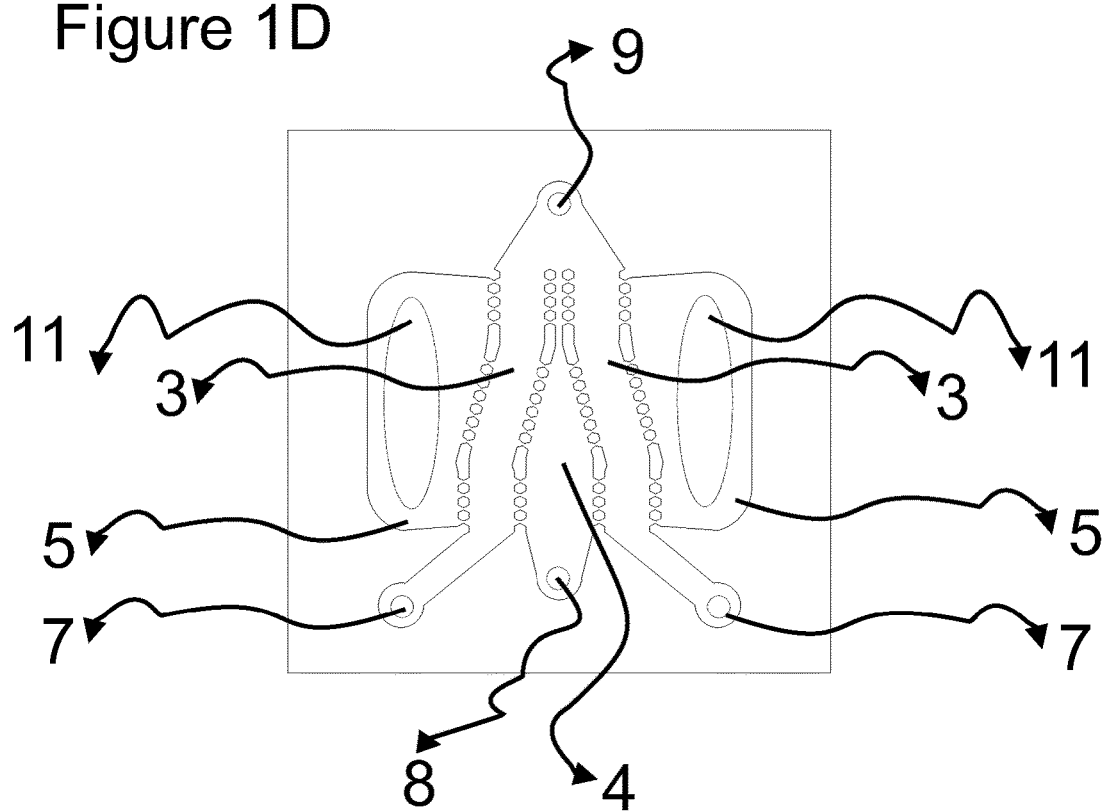
FIG. 1D shows the top view a fourth embodiment of the microfluidic device.

In another embodiment, the device has two main parts: Optically transparent surface (1) and a structure on this optically transparent surface. This structure (2) comprises, separated by posts (6), two test channels (3), one main channel (4), the width of which can be constant at different regions and increases continuously or in steps along its length in one direction, neighboring and in the middle of the test channels (3), two fluid reservoirs (5) each neighboring a test channel (3), two test channel openings (7), one main channel opening (8), one shared test and main channel opening (9) and two wide fluid reservoir openings (11) (FIG. 1D).

While the width of the main channel (4) can be constant at different places, it increases continuously or in steps along its length in one direction. Thus, components in test channels (3) are positioned at different distances from each other.

While the width of the main channel (4) can be constant at different places, it increases continuously or in steps along its length in one direction; The width of the main channel can be between 20 micrometers and 50 millimeters.

The widths of the test channels (3) can be between 50 micrometers and 10 millimeters.

The lengths of the test channels (3) and main channel (4) can be same or different, between 500 micrometers and 20 centimeters.

Test channels (3), main channel (4) and fluid reservoirs (5) of the device comprise of openings (7, 8, 9, 10, 11) that allow for loading of culture medium, physiological butler solution, one or more biological molecule or chemical, cell laden matrix, cell free matrix or a combination thereof and allow for exit of air or previously loaded material during loading. Test channel (3) and main channel (4) openings can be shared (9) or separate (7, 8) (FIGS. 1A, 1B, 1C and 1D).

The heights of fluid reservoirs (5), test channels (3) and main channel (4) can be same or different. The heights can be between 50 micrometers and 50 millimeters (FIG. 3).

Test channels (3), main channel (4) and posts (6) have the same height which can be between 50 micrometers and 1 centimeter.

Fluid reservoirs (5) can comprise of a single wide fluid reservoir opening (11) which can be as large as the fluid reservoir (5). Since the wide fluid reservoir opening (11) is large, fluids can be more easily changed.

Figure 2:
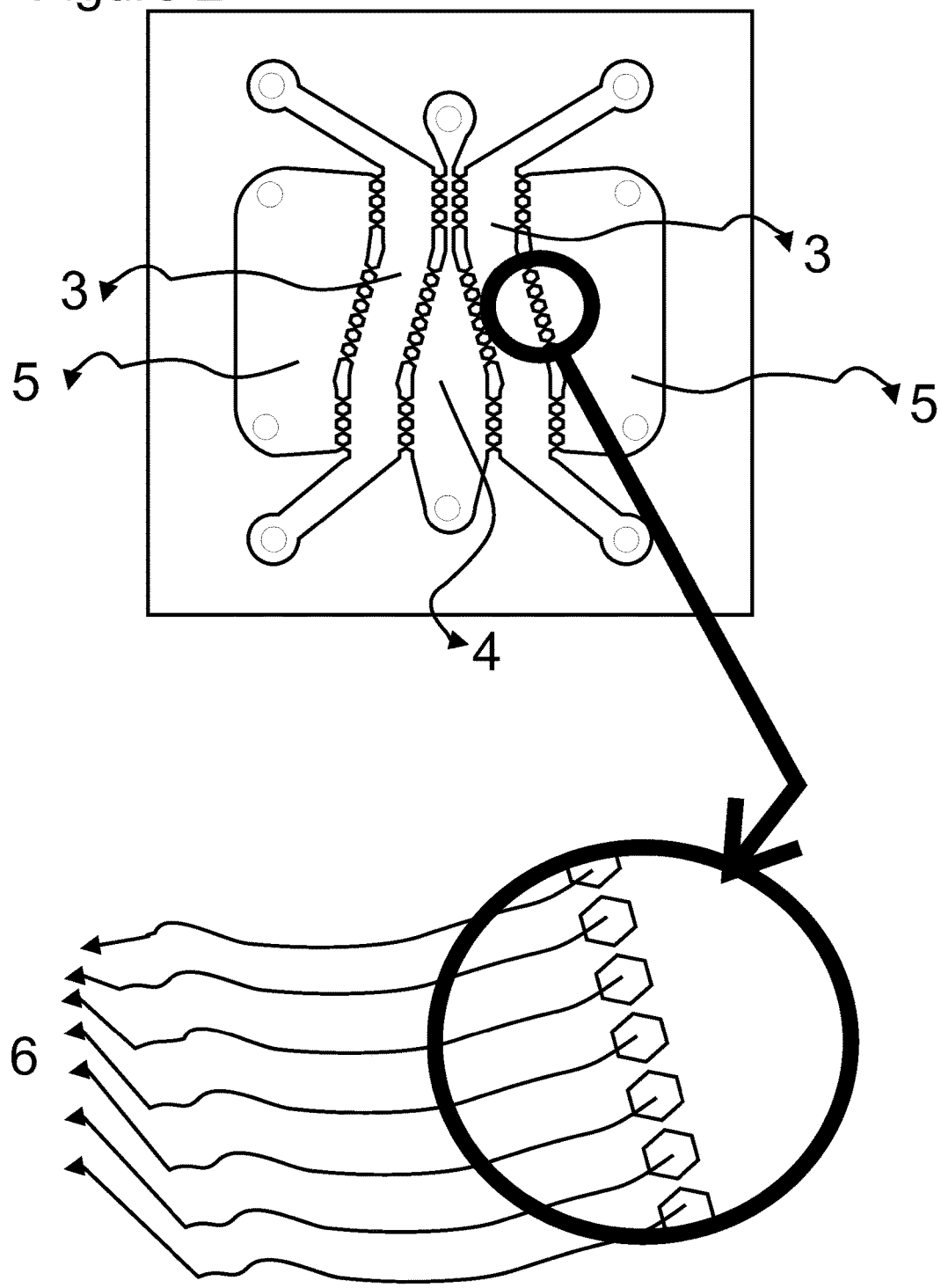
FIG. 2 shows the posts of the microfluidic device.

Test channels (3) and main channel (4) of the device are separated from each other by arrays of posts (6) (FIG. 2). Fluid reservoirs (5) are also separated from test channels (3) by arrays of posts. In each array, there is a plurality of posts (6). Since separation of channels (3, 4) and fluid reservoirs (5) from each other is realized by arrays of posts instead of continuous walls, factors in a channel (3, 4) and/or fluid reservoirs (5) can pass into other channels (3, 4) and/or fluid reservoirs (5).

Cross section of each post (6) can be hexagon, circle, ellipse or as different shape.

The horizontal long axis of each post (6) can be between 10 micrometers and 10 millimeters. The distance between two consecutive posts (6) is shorter than widths of the test channels (3) and main channel (4) they surround.

Test channel openings (7), main channel openings (8), shared test and main channel openings (9), fluid reservoir openings (10), wide fluid reservoir openings (11) of the device can have different shapes and horizontal long axis lengths between 50 micrometer and 50 millimeters The matrix in the main channel (4) and test channels (3) can be same or different. Matrices used in the device can be matrigel, collagen, laminin, agarose, polyacrylamide or biocompatible matrices or a combination thereof.

When more than one device is used devices can have separate optically transparent surfaces (1) or the structures (2) can be organized on a shared optically transparent surface (1).

The optically transparent surface (1) is the base of the device (FIG. 3). The material of the optically transparent surface (1) can be glass, polydimethylsiloxane (PDMS), polystyrene (PS) or cyclic olefin copolymer (COC).

The material of the structure (2) on the optically transparent surface (1) can be polydimethylsiloxane (PDMS) or polystyrene.

The structure (2) on the optically transparent surface (1) can be fabricated by polymerizing PDMS on silicon or SU-8 masters prepared with standard lithography techniques or by polymerizing PS on PDMS masters prepared with standard lithography techniques, or by injection molding PS. The optically transparent surface (1) and the structure can be bonded using UV/ozone treatment, plasma treatment and/or heating.

The device can be used to determine whether there is a distance dependent interaction between a cell type and a factor. Here the factor can be cells which are matrix embedded or not and same type of cells which are matrix embedded or not, another type of cells which are matrix embedded or not, different and more than one type of cells which are matrix embedded or not, a matrix with different stiffness, a different type of matrix, culture medium, physiological buffer solution, a biological or chemical molecule, a soluble or matrix bound component or a combination thereof. First cell laden matrix, cell free matrix, culture medium, physiological buffer solution or one or more biological or chemical molecule(s) or a combination thereof is loaded to the main channel (4). Then cells which are matrix embedded or not are loaded into a test channel (3) on one side of the main channel (4). Subsequently, a factor is loaded into the test channel (3) on the other side of the main channel (4). The matrix in the main channel (4) can be same as or different from the matrix in the test channels (3). Lastly,culture medium or physiological buffer solutions are loaded into the fluid reservoirs (5).

Loading of the test channels (3) and main channel (4) can also be carried out simultaneously. Loadings can be carried out into an empty device or a device previously loaded with culture medium or physiological buffer solution.

If there is an interaction between a certain cell type and a factor, that is inversely related to the distance between them, this interaction will be observed most evidently at the device position where the distance between the cells and the factor is minimum while the interaction will be much less pronounced or not observed at all at the device position where the distance between the cells and the factor is maximum. If the interaction between a certain cell type and the factor shows a positive or a negative correlation, this indicates that there is a distance dependent interaction. The interaction between the certain cell type and the factor can exhibit itself as the migration of the certain type of cell, cell viability, expression of different genes, shape change etc.

A sample application is as follows:

A certain type of cells are embedded in a matrix is loaded into the test channel (3) on one side of the main channel (4), a different type of cells embedded in a matrix are loaded in the other test channel (3) on the other side of the main channel (4). Cell free matrix is loaded into the main channel (4). Culture medium or physiological buffer solution is loaded into the fluid reservoirs (5). If there is a paracrine interaction between the two cell types and a chemotactic response, it is expected that the response changes inversely proportional to the distance between them.

Another sample application is as follows:

A certain type of cells are embedded in a matrix is loaded into the test channel (3) on one side of the main channel (4), a different type of cells embedded in a matrix are loaded in the main channel (4). Cell free matrix is loaded into the test channel (3) on the other side of the main channel (4). Culture medium or physiological buffer solution is loaded into the fluid reservoirs (5). If the cells in the main channel (4) show a feature only at the contact areas with the test channel (3) containing the other cell type, this indicates a paracrine interaction between the cell types.

Another sample application is as follows:

Cell free matrix is loaded into the test channels (3) on both sides of the main channel (4). A certain type of cells are embedded in a matrix is loaded into the main channel (4). Culture medium or physiological buffer solution is loaded into the fluid reservoirs (5). In this case, the cell density in the main channel (4) is same but there are more cells where the main channel (4) is widest. If cells in the main channel (4) show a feature most prominently at the region where the test channels (3) are furthest away from each other, then this indicates that cells have an autocrine interaction.

Another sample application is as follows:

A certain type of cells are embedded in a matrix is loaded into the test channel (3) on one side of the main channel (4), the same type of matrix without cells is loaded in the main channel (4). A matrix with different stiffness is loaded into the test channel (3) on the other side of the main channel (4). Culture medium or physiological buffer solution is loaded into the fluid reservoirs (5). If cells sense the stiff matrix in a manner dependent on the distance between the cells and the stiff matrix, the cell response, which can be differentiation, migration etc., is expected to change with the distance to the matrix with different stiffness.

The device can be used to determine whether an agent interferes with the distance dependent interaction between a certain cell type and a factor. Here the factor can be cells which are matrix embedded or not and same type of cells which are matrix embedded or not, another type of cells winch are matrix embedded or not, different and more than one type of cells which are matrix embedded or not, a matrix with different stiffness, a different type of matrix, culture medium, physiological buffer solution, a biological or chemical molecule, a soluble or matrix bound component or a combination thereof. Here the agent can be one or more drugs, a biological molecule or chemical or a combination thereof. First, cell laden matrix, cell free matrix, culture medium, physiological buffer solution or one or more biological or chemical molecule(s) or a combination thereof is loaded to the main channel (4) Then cells which are matrix embedded or not are loaded into a test channel (3) on one side of the main channel (4). Subsequently, a factor is loaded into the test channel (3) on the other side of the main channel (4). The matrix, in the main channel (4) can be same as or different from the matrix in the test channels (3). Lastly, culture medium or physiological buffer solutions are loaded into the fluid reservoirs (5). In addition, the agent to be tested is added to the contents of one or more of the test channels (3), the main channel (4) and fluid reservoirs (5). Loading of the test channels (3) and main channel (4) can also be carried out simultaneously. Loadings can be carried out into an empty device or a device previously loaded with culture medium or physiological buffer solution. If the tested agent reduces or enhances the interaction between the certain cell type and the factor, then this indicates that the tested agent can change the distance dependent interaction between the certain cell type and the factor.

A sample application is as follows:

A certain type of cells are embedded in a matrix is loaded into the test channel (3) on one side of the main channel (4), a different type of cells embedded in a matrix are loaded in the other test channel (3) on the other side of the main channel (4). Collagen containing an agent to be tested, for instance chemical molecule, is loaded into the main channel (4). If while one of the cell types migrates towards the other in the absence of the agent, and there is no migration in the presence of the agent, then this indicates that the agent inhibits the distance dependent interaction between the two cell types.

Any cell line and/or primary cells and/or biopsy cells can be used in the device.

The invention claimed is:

1. A microfluidic device comprising
   an optically transparent surface, and
   a structure in the optically transparent surface comprising;
      at least two test channels,
      a main channel, which is between the two test channels and the width of which is constant at different regions and increases continuously or in steps along its length in one direction,
      two fluid reservoirs, each of which neighbors one of the test channels, a plurality of borders comprising a plurality of posts that separate the test channels from the main channel and from the fluid reservoirs,
      at least two test channel openings, and
      at least one main channel opening.

2. The microfluidic device of claim 1, wherein the fluids in the fluid reservoirs comprise of a culture medium, a physiological buffer solution, one or more biological molecule, chemical or a combination thereof.

3. The microfluidic device of claim 1, wherein the test channels, the main channel, and the fluid reservoirs comprise of openings that allow for loading of culture media, physiological buffer solutions, one or more biological or chemical molecule, cell laden matrices, cell free matrices or a combination thereof and that allow for exit of air or previously loaded material during loading.

4. The microfluidic device of claim 1, wherein the test channels, the main channel and the posts are the same height.

5. The microfluidic device of claim 1, wherein the heights of the test channels, the main channel and the posts are between 50 micrometers and 1 centimeter.

6. The microfluidic device of claim 1, wherein the test channels and the main channel are the same lengths.

7. The microfluidic device of claim 1, wherein the test channels and the main channel have different lengths.

8. The microfluidic device of claim 1, wherein each length of the test channels and the main channel are between 500 micrometers and 20 centimeters.

9. The microfluidic device of claim 1, wherein the material of the optically transparent surface is polydimethylsiloxane (PDMS), polystyrene (PS) or cyclic olefin copolymer (COC).

10. The microfluidic device of claim 1, wherein the material of the structure is polyilimethylsiloxane (PDMS), polystyrene (PS) or cyclic olefin copolymer (COC).

11. A method of determining whether there is a distance dependent interaction between a certain type of cell and a factor comprising:

simultaneous or consecutive loading of cells, which are matrix embedded or not, into one of the test channels on one side of the main channel of the microfluidic device in claim 1, loading of a factor into the other test channel on the other side of the main channel of the microfluidic device in claim 1, loading of cell laden or cell free matrix, culture medium, physiological buffer solution, one or more biological molecule or chemical or a combination thereof into the main channel of the microfluidic device in claim 1, loading of culture medium or physiological buffer solution into the fluid reservoirs of the microfluidic device in claim 1, incubating the device at appropriate cell culture conditions and determining whether there is a distance dependent interaction between the components of the two test channels of the microfluidic device in claim 1, wherein if the interaction of the cells, which are matrix embedded or not, with the factor shows a positive or negative correlation, then this indicates that there is a distance dependent interaction.

12. The method of claim 11, wherein the factor comprises same type of cells which are matrix embedded or not, different type of cells which are matrix embedded or not, different and more than one type of cells which are matrix embedded or not, a matrix with different stiffness, a different type of matrix, culture medium, physiological buffer solution, a biological or chemical molecule or a combination thereof.

13. A method of determining whether an agent interferes with the distance dependent interaction of cells, which are matrix embedded or not, with a factor, comprising simultaneous or consecutive loading of cells, which are matrix embedded or not, into one of the test channels on one side of the main channel of the microfluidic device in claim 1, loading of a factor into the other test channel on the other side of the main channel of the microfluidic device in claim 1, loading of cell laden or cell free matrix, culture medium, physiological buffer solution, one or more biological molecule or chemical or a combination thereof into the main channel of the microfluidic device in claim 1, loading of culture medium or physiological buffer solution into the fluid reservoirs of the microfluidic device in claim 1, addition of the agent to be tested to one or more of the components of the test channels, main channel and /or fluid reservoirs of the device in claim 1 during initial loading or afterwards, incubating the device at appropriate cell culture conditions, and determining whether a distance dependent interaction changed or not;

wherein if the distance dependent interaction increases or decreases, then this indicates that the agent tested changes the distance dependent interaction between the cells, which are matrix embedded or not, and the factor.

14. The method of claim 13, wherein the factor comprises same type of cells which are matrix embedded or not, different type of cells which are matrix embedded or not, different and more than one type of cells which are matrix embedded or not, a matrix with different stiffness, a different type of matrix, culture medium, physiological buffer solution, a biological or chemical molecule or a combination thereof.

15. The method of claim 13 wherein the agent comprises one or more drugs, a biological molecule or chemical or a combination thereof.

* * * * *